US005092859A

United States Patent [19]

[11] Patent Number: 5,092,859

Everett et al.

[45] Date of Patent: Mar. 3, 1992

[54] ONE PIECE COLLAPSIBLE UROLOGY DRAIN PAN

[75] Inventors: Dennis K. Everett, Garfield Heights; Charles G. Cassudakis, Mentor; Kenneth M. Haney, Newbury, all of Ohio

[73] Assignee: Picker International, Inc., Highland Hts., Ohio

[21] Appl. No.: 615,878

[22] Filed: Nov. 20, 1990

[51] Int. Cl.[5] .............................................. A61M 1/00

[52] U.S. Cl. .................................... 604/322; 128/760

[58] Field of Search ........................ 604/322; 128/760; 220/480, 481, 482, 657, 659; 5/503; 232/433

[56] References Cited

U.S. PATENT DOCUMENTS 3,268,144 8/1966 Gaunt ................................ 220/659

4,880,418 11/1989 Tramont ............................ 604/356

4,936,836 6/1990 Weickgenannt .................... 604/322

FOREIGN PATENT DOCUMENTS 571577 11/1943 United Kingdom ................. 220/18

*Primary Examiner*—Randy C. Shay

*Assistant Examiner*—G. Gualtieri

*Attorney, Agent, or Firm*—Fay, Sharpe, Beall, Fagan, Minnich & McKee

[57] ABSTRACT

A one piece plastic drain pan (24) is mounted to an examination end (14) of a urology table (10). The pan includes an integrally constructed vertical inner end wall (28), a sloping outer end wall (34), a pair or opposite side walls (30), (32), and a bottom wall (36) through which a drain port (38) is defined. The plastic material, particularly in the side walls has sufficient plastic memory that as a physician leans against the outer end wall (34), the side walls bow outward compressing the end walls toward each other. When the pressing force is removed, the end walls return themselves to the non-flexed position and the end walls move apart. Plates (50, 52) clamp the inner end wall (28) of the plastic drain pan securely therebetween. The plates have flanges (54) which are received in mating slots (56) in the examination end (14) of the urology table. A folding screen arrangement (60) provides a convenient storage surface for examination tools and separates stones, tissue, and the like from drained fluids. The drain pan has integrally connected horizontal flanges (42, 44) adjacent the side walls and a rolled flange along the outer end wall.

15 Claims, 5 Drawing Sheets

ONE PIECE COLLAPSIBLE UROLOGY DRAIN PAN

BACKGROUND OF THE INVENTION

The present invention relates to constructions for draining fluid during urology examinations.

In the past, rigid, stainless steel drain pans were connected to one end of a urology examination table to capture urine, fluids used during irrigation, tissue dislodged during urological procedures, and the like. One of the problems with rigid urology pans is that they were mounted on the examination end of the table, i.e. between the physician and the patient. The physician frequently found it necessary to lean into and reach across the drain pan during examinations and procedures. The rigid pans were uncomfortable to the physician and interfered with performance of medical procedures.

Another urology drain arrangement is illustrated in U.S. Pat. No. 4,936,836. In this patent, a complex arrangement of stainless steel frame pieces are pivotally interconnected and biased into an open rectangle by springs in the hinges. A disposable, light weight, flexible urology bag is hung on and supported by the pivotal frame members. One of the problems with this arrangement is that the mechanical frame mechanism is relatively expensive and complex. Moreover, the numerous surfaces and moving parts make the frame assembly difficult to clean. The one time used disposable drain bags present another problem. Not only are the bags costly, but they also create inventory and storage problems.

In another arrangement, a flexible steel band is mounted to the end of the urology table. A light weight, disposable urology bag is hung from and supported by the steel band. Although the steel band is much less costly and simpler to clean than the complex hinged frame arrangement, the disposable bags are still costly and present inventory and storage problems.

The present invention contemplates a new and improved urology drain assembly which overcomes the above-referenced problems and others.

SUMMARY OF THE INVENTION

In accordance with one aspect of the present invention, a one piece, plastic urology drain pan is provided. The pan is constructed of a sufficiently strong, stiff plastic that is self-supporting, yet sufficiently flexible at least along its vertical sides that as the physician leans forward, the pan flattens and has less horizontal extension.

In accordance with a more limited aspect of the present invention, the drain pan has a rigid mounting assembly along an inner elongated end for mounting to a urology table. Outward extending sides have an outward flange adjacent the top which permits the side portions to fold along a generally vertical axis along a U-shaped horizontal cross section. An outer elongated end has a rolled, more rigid flange which is engaged by the physician as the physician leans forward.

One advantage of the present invention is that it is reusable and readily cleaned.

Another advantage of the present invention is that it is relatively inexpensive.

Another advantage of the present invention is that it eliminates the inventory and storage problems of disposable urology drain bags.

Another advantage of the present invention is that it is comfortable to the physician and moves easily as the physician leans into it.

Still further advantages of the present invention will become apparent to those of ordinary skill in the art upon reading and understanding the following detailed description.

BRIEF DESCRIPTION OF THE DRAWINGS

The invention may take form in various parts and arrangements of parts, and in various steps or arrangements of steps. The drawings are only for purposes of illustrating a preferred embodiment and are not to be construed as limiting the invention.

DETAILED DESCRIPTION OF THE PREFERRED EMBODIMENT

Figure 1:
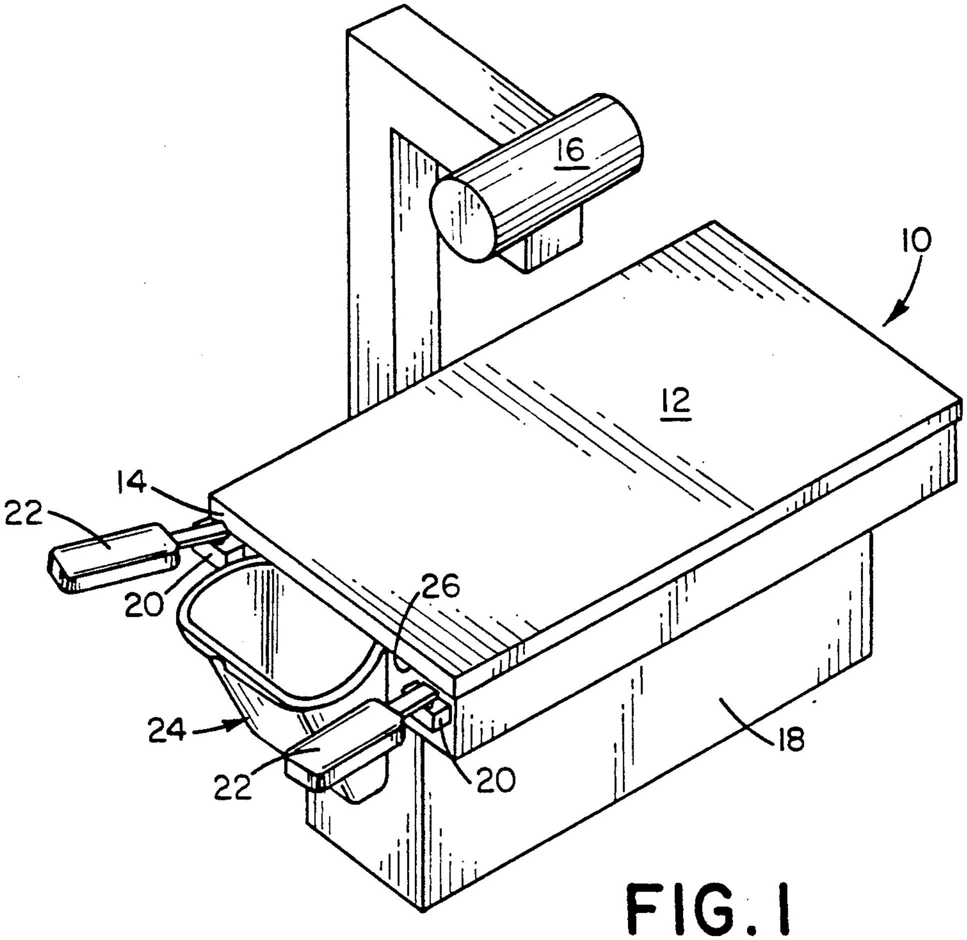
FIG. 1 is a diagrammatic illustration of a urology table and drain bag in accordance with the present invention.

With reference to FIG. 1, a urology table 10 has a patient supporting top or surface 12 that terminates toward an examination end 14. An x-ray tube or unit 16 is disposed above the patient supporting surface 12. X-ray detectors (not shown) are mounted in a table top supporting base 18 to receive radiation from the x-ray tube. In a fluoroscopy mode, low level radiation is emitted from the x-ray tube, passes through the patient and table top, and is received by the detectors. The detected radiation is converted into continuous display on a CRT or video monitor (not shown). In a radiography mode, the x-ray tube is operated at a higher energy to produce a higher contrast image either with the x-ray detectors or by exposing radiographic film.

The urology table lo has mounting assemblies 20 for pivotally mounting a pair of elbow supports 22 at the examination end 14 of the table. A urology pan 24 is removably mounted to the examination end 14 by a drain pan mounting means 26.

Figure 2:
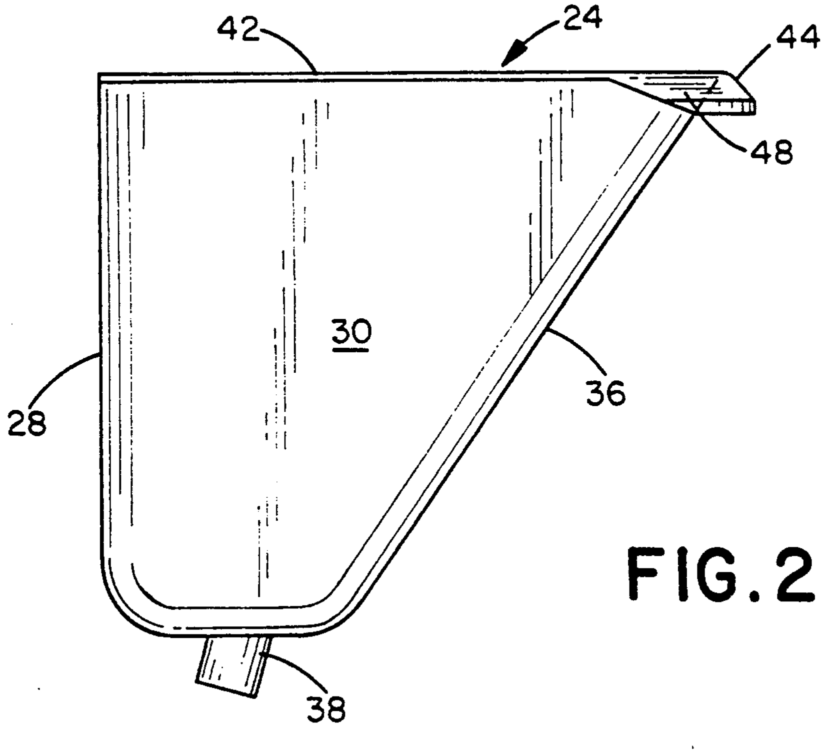
FIG. 2 is a side view of the urology pan of FIG. 1.
Figure 4:
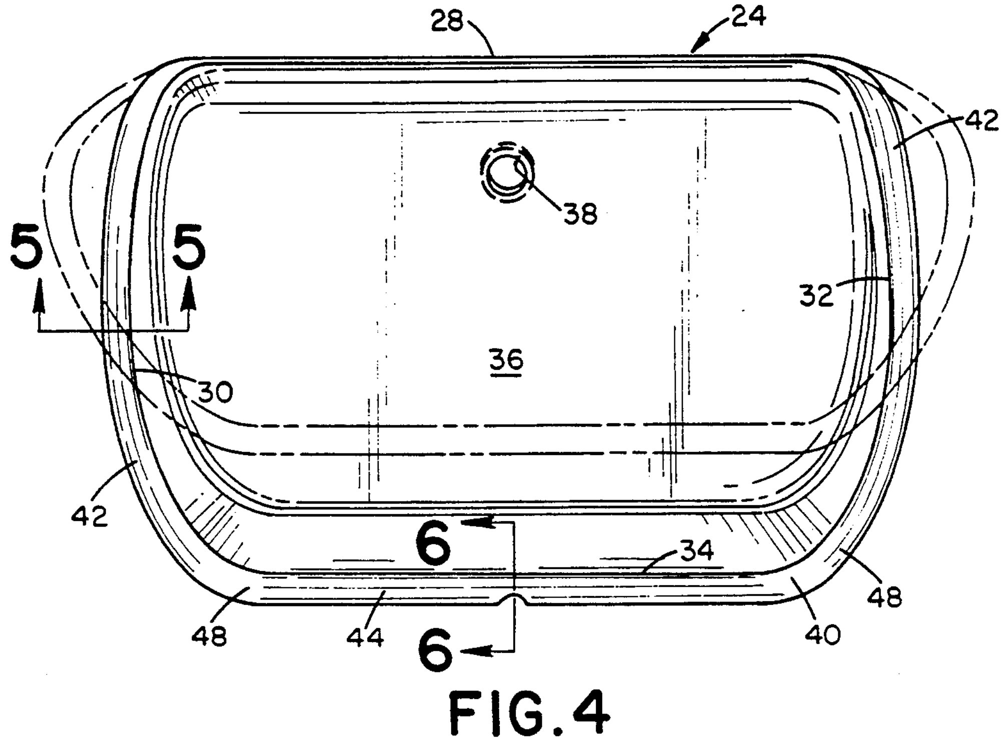
FIG. 4 is a top view of the urology pan.
Figure 3:
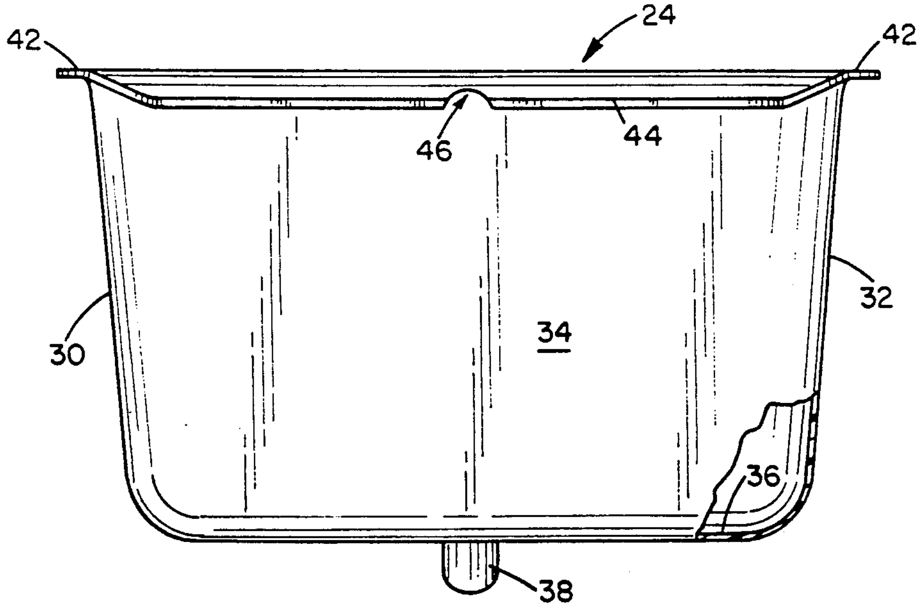
FIG. 3 is a front view of the urology pan.

With reference to FIGS. 2, 3, and 4, the urology pan has a generally vertical, flat inner end wall 28. A pair of side walls 30, 32 are integrally connected with the inner end wall. A sloping outer end wall 34 and a bottom wall 36 are integrally connected to the side and front walls. A drain nipple 38 is provided in the bottom wall to receive a drain hose. In the preferred embodiment, the drain pan is constructed of polyethylene, although other plastics and flexible materials are contemplated.

Figure 5:
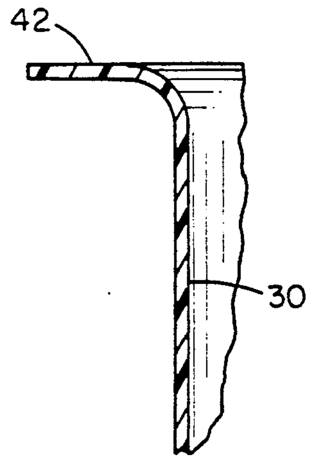
FIG. 5 is a sectional view through section 5—5 of FIG. 4.

With continuing reference to FIGS. 2–4 and further reference to FIG. 5, a flange 40 extends outward from the side walls 30 and 32 and the outer end wall. The side walls and a horizontal flange portion along the sides are configured such that the side walls can bow outward in a generally U-shaped horizontal cross section as illustrated in phantom in FIG. 4. More particularly, the horizontal side flange portions tend to flex upward and more into alignment with the side walls as the side walls are flexed. The horizontal flange stiffens a spring constant or plastic memory of the side walls and provides greater rigidity and support.

Figure 6:
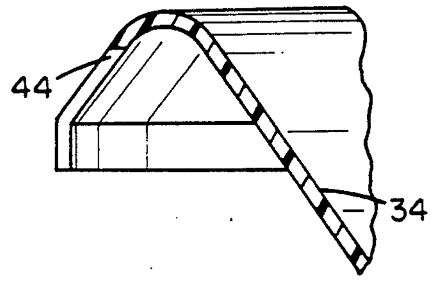
FIG. 6 is a sectional view through section 6—6 of FIG. 5.

With continuing reference to FIGS. 2–4 and further reference to FIG. 6, the flange 40 includes a U-shaped or rolled flange portion 44 that extends along the upper edge of the outer end wall 34. The outer wall flange portion 44 rolls downward to provide greater rigidity. A cutout 46 generally centrally in the outer flange portion 44 allows limited flexing and prevents buckling of the outer flange portion as the outer end wall 34 flexes trying to conform to the rounded contours of the urologist's stomach. At a transition area between the end and side walls, the flange has a transition portion 48 tapers from the horizontal cross section of FIG. 5 to the rolled cross section of FIG. 6.

The mounting means 26 includes a pair of plates 50 and 52 which frictionally engage and lock the drain pan inner end wall 28 therebetween. The outside plate includes a pair of projections or ears 54 on either end thereof which are received in matching slots $6 on the end face 14 of the urology table. A lip $8 limits vertical, downward movement of the plates and positioning the drain pan just below the table top. Preferably, a locking mechanism releasably locks the projects in the slots. Suitable locking mechanisms include screws or bolts, spring biased detents, slide latches, and the like.

Figure 7:
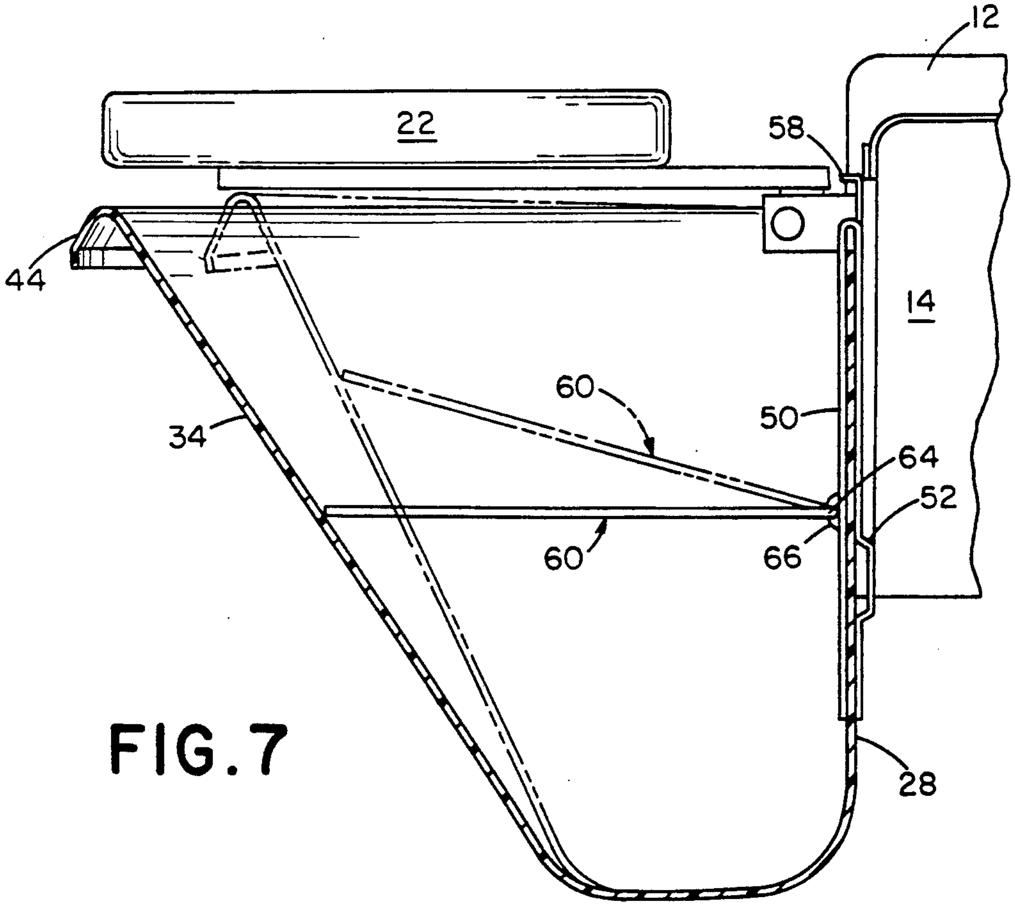
FIG. 7 is a side sectional view of the urology pan and mounting structure.
Figure 8:
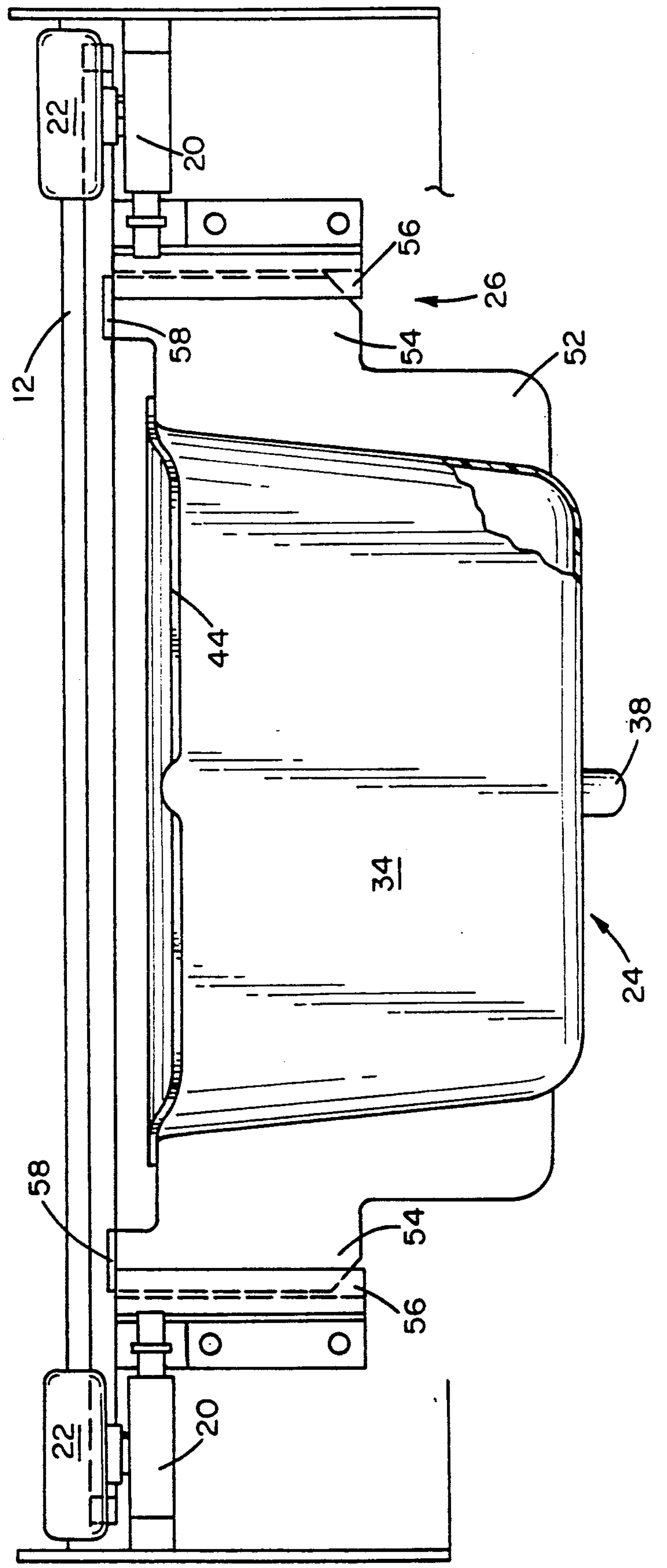
FIG. 8 is a front view illustrating structure for mounting the urology pan to the end of the examination table.
Figure 9:
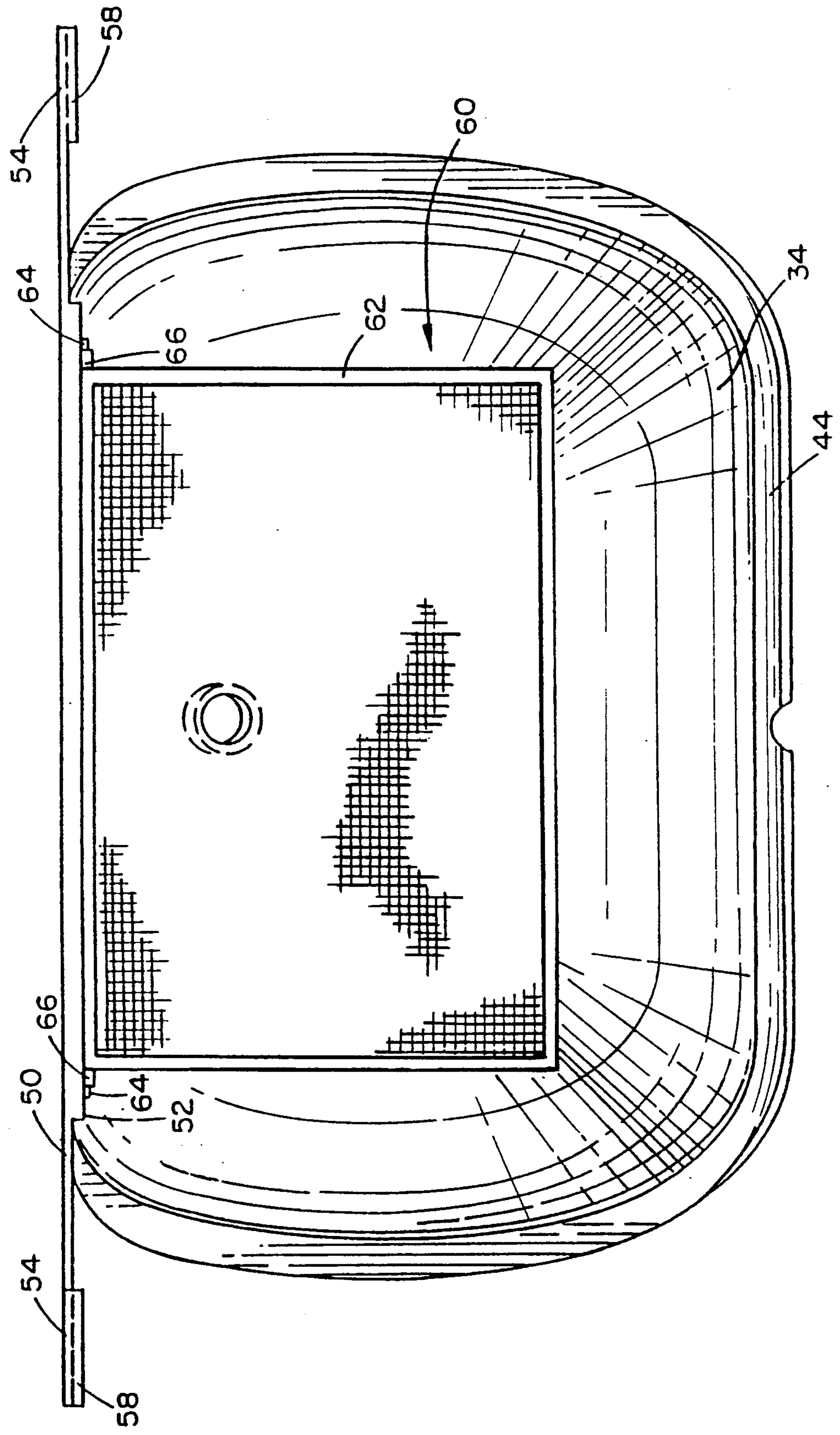
FIG. 9 is a top view of the drain pan and mounting assembly.

With continuing reference to FIG. 7 and further reference to FIG. 9, it is often advantageous to catch stones, tissue, and the like dislodged during a urological procedure. To this end, a screen or grate may be placed across the drain outlet 38. However, it is also advantageous to provide the physician a place to rest instruments. To this end, a screen assembly 60 is provided which is selectively positionable across the drain pan adjacent a central or upper portion thereof. In the illustrated embodiment, the screen includes a frame 62 with pivot points 64 that are pivotally received in slots 66 of the plate 52. The pivotal mounting enables the screen to be moved vertically and rest parallel to the inner end wall. The width of the frame and the mesh carried thereby is selected relative to the drain pan that the screen rests generally horizontally against the outer end wall 34. As the physician leans forward, contracting the drain pan, the screen is free to ride upward along the sloping outer end wall. In this manner, a screen is provided that is sufficiently high to provide a convenient resting place for instruments, yet does not interfere with compression of the drain pan.

With the present arrangement, the drain pan is readily cleaned and disinfected. The drain pan is amenable to being sprayed and washed down with a spray or squeeze bottle of liquid disinfectant or sterilant. For more thorough sterilization, the drain pan is readily removed from the end of the table for sterilization with ethylene oxide, or the like.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A urology drain pan assembly comprising:

a unitary, plastic drain pan including a generally vertical inner end wall, a pair of integrally connected self-supporting side walls, a horizontal flange extending along an upper end of the side walls, an integrally connected outer end wall, and an integrally connected bottom wall through which a drain outlet is defined, the side and end walls and the horizontal flange being constructed of plastic that has a plastic memory such that as the outer end wall is pressed towards the inner end wall, the side walls flex outward, the flange buckles permitting the side walls to flex, the memory of the plastic of the side walls and the flange provides a spring force which causes the side walls to unflex and the outer end wall to return towards its original position; and a mounting means for mounting the urology pan to an end of a urology examination table by the inner end wall such that the outer end wall is supported by the side walls which are supported by the inner end wall.

2. The apparatus as set forth in claim 1 further including a means for pivotally mounting an elbow support, the elbow support mounting means being mounted to the urology table end wall.

3. The assembly as set forth in claim 1 wherein the outer end wall tapers outward from the bottom wall towards a top edge thereof and further including a screen which is pivotally connected adjacent the inner end wall and which rests, generally horizontally against the sloping outer end wall, such that as the outer end wall is pressed toward the inner end wall, the pivotally connected screen pivots upward and rides therealong.

4. A urology drain pan assembly comprising:

a unitary, plastic drain pan including a generally vertical inner end wall;

a mounting means for mounting the inner end wall to an end of a urology examination table, the mounting means including:

an interior plate, an exterior plate connected and disposed closely parallel to the interior plate such that the inner end wall is clamped securely therebetween, the exterior plate having outward extending tabs which are received in slots defined on the urology table end wall;

the drain pan further including:

a pair of side walls integrally connected to and supported by the inner end wall, an outer end wall integrally connected to and supported by the side walls, an integrally connected bottom wall through which a drain outlet is defined, the end walls being constructed of plastic that has a plastic memory such that as the outer end wall is pressed towards the inner end wall, the side walls flex, the memory of the plastic of the side walls causes the side walls to unflex and biases the outer end wall to return towards its original position.

5. The assembly as set forth in claim 4 wherein the exterior plate further defines a stop for limiting vertical receipt of the tabs into the slots.

6. The assembly as set forth in claim 4 wherein the drain pan further includes a horizontal flange extending along an upper end of the side walls, whereby as the side walls are flexed outward, the flange flexes into alignment with the end walls permitting the end walls to flex, and wherein the memory of the plastic of the flange provides a spring force to assist in returning the end walls to an unflexed position.

7. The assembly as set forth in claim 6 further including a rolled flange integrally connected with an upper edge of the outer end wall to resist flexing of the outer end wall.

8. A urology drain pan assembly comprising:

(a) a unitary, plastic drain pan including:

a generally vertical inner end wall, a pair of integrally connected side walls, an integrally connected outer end wall, the end walls being constructed of plastic that has a plastic memory such that as the outer end wall is pressed towards the inner end wall, the side walls flex, the memory of the plastic of the side walls causes the side walls to unflex and the outer end wall to return toward its original position, a horizontal flange extending along an upper end of the side walls, a rolled flange integrally connected with an upper edge of the outer end wall to resist flexing of the outer end wall, a notch is defined in a central portion of the outer end wall flange to facilitate the outer end wall flexing inward to contour to a stomach of a physician pressing thereagainst, an integrally connected bottom wall through which a drain outlet is defined; and (b) a mounting means for mounting the inner end wall to an end of a urology examination table.

9. The assembly as set forth in claim 8 further including a transition flange portion integrally connected with the horizontal side flange and the rolled end flange for providing a smoother transition therebetween.

10. A urology drain pan assembly comprising:

a unitary, plastic drain pan including a generally vertical inner end wall, a pair of integrally connected self-supporting side walls, an integrally connected outer end wall supported by the side walls, and an integrally connected bottom wall through which a drain outlet is defined, the end walls being constructed of plastic that has a plastic memory such that as the outer end wall is pressed toward the inner end wall, the side walls flex, the memory of the plastic of the side walls causes the side walls to unflex and the outer end wall to return towards its original position; and a mounting means for mounting the inner end wall to an end of a urology examination table, the mounting means including:

an interior plate, an exterior plate connected to the inner plate such that the interior and exterior plates frictionally engages the inner end wall therebetween, the interior plate having a pair of hinge pin receiving recesses; and a screen having a pair of hinge pins removably received in the recesses, such that the screen is removable.

11. A flexible, reusable urology pan assembly comprising:

a one piece plastic pan having an inner end wall, opposite side walls which are selectively compressible in a horizontal direction, the plastic of which the opposite side walls are made having sufficient plastic memory that after a compressing force is removed, the plastic pan returns substantially to its original shape, an outer end wall supported by the side walls, the end and side walls having sufficient structural rigidity that the pan is self-supporting, a bottom wall of the pan defining a drain outlet port therein;

a pair of metal plates which frictionally clamp the inner end wall therebetween;

a mounting means for mounting the plates to an end wall of a urology table.

12. The assembly as set forth in claim 11 further including a flange extending continuously along upper edges of the side and outer end walls.

13. A flexible, reusable urology pan assembly comprising:

a one piece plastic pan having an inner end wall, opposite side walls, and an outer end wall, the side walls having sufficient flexibility that as the opposite side walls are selectively compressed in a horizontal direction, plastic in the opposite side walls has sufficient plastic memory that after the compressing force is removed, the plastic pan returns substantially to its original shape, the end and side walls having sufficient structural rigidity that the pan is self-supporting, a bottom wall of the pan defining a drain outlet port therein the outer end wall tapering outward from the bottom wall towards a top edge thereof a rigid screen which is pivotally connected adjacent the inner end wall and which rests, generally horizontally against the sloping outer end wall, such that as the outer end wall is pressed toward the inner end wall, the pivotally connected screen pivots upward and slides along the outer end wall toward a more vertical orientation;

a metal plate extending along and secured to the inner end wall;

a mounting means for mounting the plate to an end wall of a urology table.

14. A flexible, reusable urology pan assembly comprising:

a one piece plastic pan having an inner end wall, opposite side walls, and an outer end wall, the side walls having a sufficient flexibility that the opposite side walls are selectively compressible in a horizontal direction, plastic in the opposite side walls having sufficient plastic memory that after a compressing force is removed, the plastic pan returns substantially to its original shape, the end and side walls having sufficient structural rigidity that the pan is self-supporting, a flange extending continuously along upper edges of the side and outer end walls, the flange being generally horizontal adjacent at least a mid-portion of the side walls and bending downward along at least a portion of the outer end wall, a bottom wall of the pan defining a drain outlet port therein;

a metal plate extending along and secured to one end wall;

a mounting means for mounting the plate to an end wall of a urology table.

15. An apparatus comprising:

a urological table defining an examination end;

a one piece self-supporting plastic drain pan having a generally vertically inner end and an outer end which are integrally connected with opposite side walls and a bottom wall through which an outlet port is defined, the drain pan having sufficient strength so as to be self-supporting, yet sufficiently flexible that the side walls flex outward as the end walls are pressed together and after the pressing force is removed, plastic memory of the pan causes the side walls to unflex and the end walls to move apart;

a mounting means for mounting only the inner end wall vertically to the examination end of the urological table such that the side walls are supported by the inner end wall and themselves and the outer end wall is supported by the side walls.

* * * * *